United States Patent

Wess

[11] Patent Number: 5,795,311
[45] Date of Patent: Aug. 18, 1998

[54] APPARATUS FOR THE TREATMENT OF BIOLOGICAL TISSUE AND CORPORAL CONCRETIONS

[75] Inventor: Othmar Wess, Lendwll-Oberhofan, Switzerland

[73] Assignee: Storz Medical AG, Switzerland

[21] Appl. No.: 553,696

[22] PCT Filed: Jun. 1, 1994

[86] PCT No.: PCT/EP94/01784

§ 371 Date: Jun. 17, 1996

§ 102(e) Date: Jun. 17, 1996

[87] PCT Pub. No.: WO94/28540

PCT Pub. Date: Dec. 8, 1994

[30] Foreign Application Priority Data

Jun. 1, 1993 [DE] Germany ............... 43 18 237.2

[51] Int. Cl.⁶ .................................................. A61B 17/22
[52] U.S. Cl. .................................................. 601/2; 601/4
[58] Field of Search ............... 601/2–4; 128/662.03, 128/662.06, 663.01, 660.03; 606/1; 600/439

[56] References Cited

U.S. PATENT DOCUMENTS

| | | |
|---|---|---|
| 4,207,901 | 6/1980 | Nigam .................. 128/663.01 |
| 4,562,900 | 1/1986 | Anderson et al. . |
| 4,893,624 | 1/1990 | Lele ............................ 601/3 |
| 4,936,303 | 6/1990 | Detwiler et al. ............ 601/3 |
| 5,402,792 | 4/1995 | Kimura ..................... 600/472 |

FOREIGN PATENT DOCUMENTS

| | | |
|---|---|---|
| 0369 177 | 10/1988 | European Pat. Off. . |
| 0434931 | 7/1991 | European Pat. Off. . |
| 2919176 | 11/1980 | Germany . |
| 3040635 | 5/1982 | Germany . |
| 3727692.1 | 3/1989 | Germany . |
| 3835318.0 | 6/1990 | Germany . |
| 284836 | 12/1952 | Switzerland . |

*Primary Examiner*—Francis Jaworski
*Attorney, Agent, or Firm*—Donald D. Mon

[57] ABSTRACT

Disclosed is an apparatus for the treatment of biological tissue as well as for destroying concretions by means of focussed acoustic waves, having

- a sound generating unit which a control unit triggers in such a manner that the unit generates acoustic waves of a specific frequency and energy, and
- a focussing unit which focusses the generated waves in a focal area.

The present invention is distinguished by the sound generating unit (2) being provided, in an as such known manner, with a plane or only slightly curved radiation area in such a manner that the generated wave is an essentially plane wave and that the focussing unit (5) disposed in a fixed spatial relationship to the sound generating unit being provided with a Fresnel lenslike structure on the sound entry and/or sound exit area.

29 Claims, 4 Drawing Sheets

AAF 036 A

AAF 037 A

AAF 038 A

APPARATUS FOR THE TREATMENT OF BIOLOGICAL TISSUE AND CORPORAL CONCRETIONS

This application is a 371 of PCT/EP 94/01784 Jun. 1, 1994.

TECHNICAL FIELD

The present invention relates to an apparatus for the treatment of biological tissue and corporal concretions using focussed acoustic waves according to the introductory part of claim 1.

STATE OF THE ART

In the course of the development of noninvasive therapeutic methods, procedures have been developed that generate a locally confined, controlled effect inside the body obviating traumatic penetration of the body. One example of this is extracorporally induced lithotripsy in which short pressure pulses of high amplitude, which are focussed on the to-be-destroyed concretion, by way of illustration a kidney stone, are generated outside the body. When the energy density is high enough at the site of the concretion, the concretion is crushed. An example of such an apparatus is described in DE 38 35 318 C1, to which, in addition to the literature cited therein, reference is explicitly made with regard to all the terms not explained in more detail herein. Furthermore, it has been proposed to utilize energy concentrated with the aid of highly energetic ultrasound waves for hyperthermy or for thermotherapy.

In all the processes in which focussed acoustic waves are employed for achieving successful therapy, it is necessary that the energy generated outside the body is coupled in exploiting suited "body windows" in the body and steered to the predetermined target area by means of suited locating procedures. It must be taken into account that many organs cannot be reached directly via suited "body windows". But rather the available body windows are of irregular shape, such as by way of illustration the window through which ultrasound can be coupled into the liver or the urinary bladder. Moreover, it is often necessary to beam in the ultrasound with a "slanted" respectively inclined direction of incidence.

The hitherto proposed sound generating units such as, by way of illustration, mentioned in DE 38 35 318 C1, i.e., by way of illustration spherical caps, concave ellipsoids or paraboloids of rotation can therefore only be employed in a restricted manner, because the circular shaped radiating areas of these sound generating units are not optimumly adapted to the body windows at disposal. Moreover, if the coupling-in direction is slanted, the coupling media can only be poorly adapted to the contours of the body.

As a consequence, only a part of the ultrasound generated outside the body is at disposal for therapeutical purposes at the target site. In addition, regional and temporal focussing is frequently insufficient due to phase disturbances on the propagation path (coupling medium and corporal tissue). Furthermore, only a certain part of the generated ultrasonic energy is released into the coupling medium, because the acoustic impedances (density $\rho$ * propagation velocity c) of the sound generator and of the tissuelike transmission respectively coupling medium (often water) are very different especially when piezo-electric exciters are used so that the energy can only be partially coupled in.

The object of the present invention is to provide an apparatus for the treatment of biological tissue using focussed acoustic waves, this apparatus being easy to adapt to the different instances of application and not being restricted to circular radiation areas.

An element of the present invention is that the sound generating unit is provided with, in an as such known manner, a plane or only minimally concave or convex curved radiation area so that the generated wave is essentially a plane wave. In order to focus this essentially plane wave, the focussing unit disposed in a fixed spatial relationship to the sound generating unit has a Fresnel lenslike structure on its sound entry and/or sound exit area. Fresnel lenses are not only already known from light optics, but have also already been proposed for ultrasonic imaging systems, by way of illustration in DE 29 19 176 C 2. Fresnel lenses of this type are designed in such a manner that coherent ultrasound at the individual segments of the lens has a phase difference of n * $\lambda$ (n=0,1,2 ... ) so that the ultrasound waves propagating through the adjacent zones of the lens interfere constructively in the focal zone when leaving the lens.

Figure 1A:
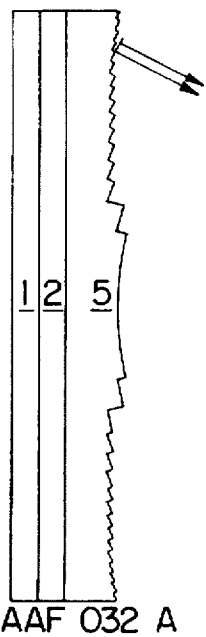
FIG. 1a shows the fundamental concept of the present invention.
Figure 1B:
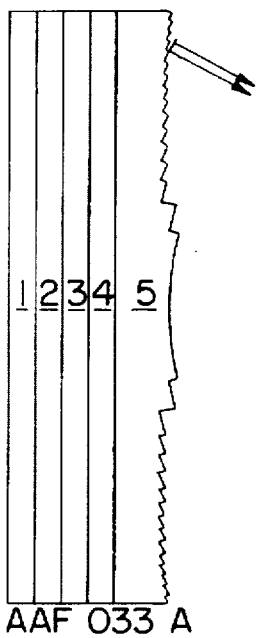
FIG. 1b shows an alternative embodiment using multiple adapting layers.
Figure 1C:
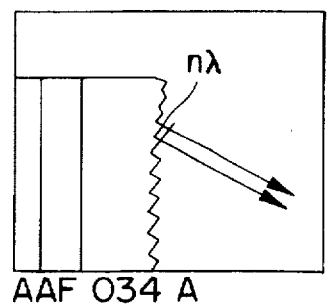
Figure 2:
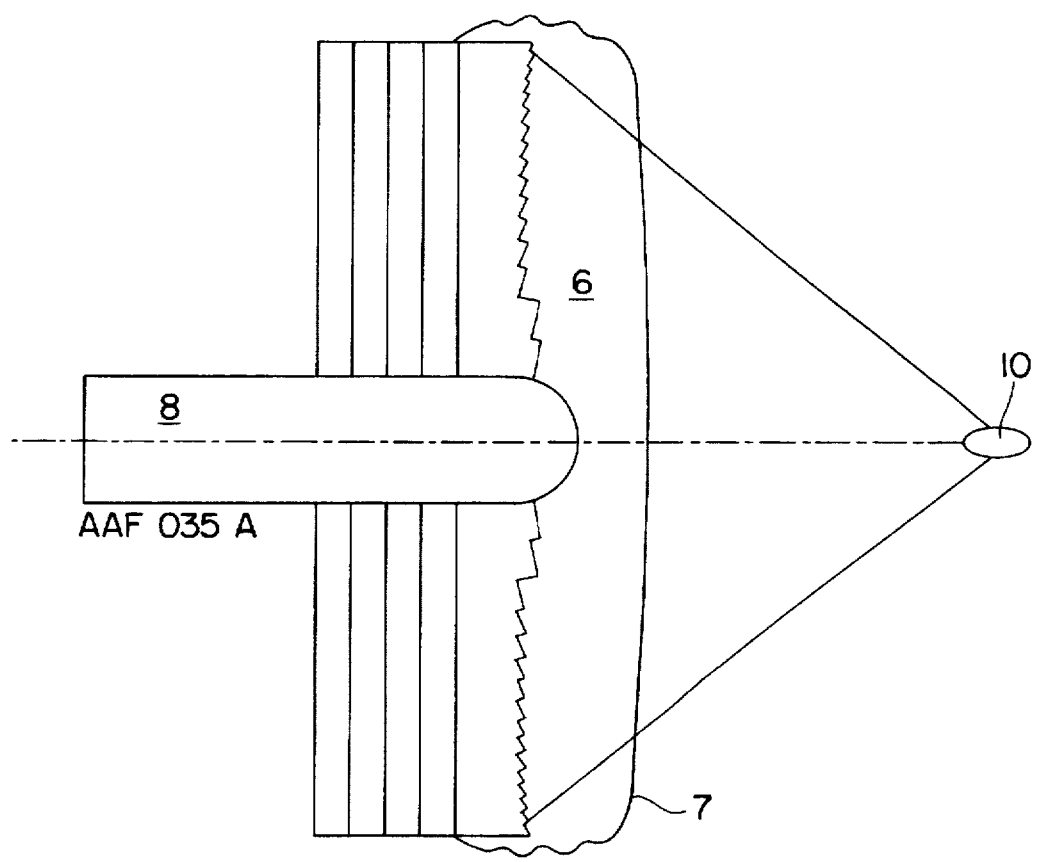
FIG. 2 shows the inventive transducer combined with a target locator device.

The fundamental concept of the present invention is explained using FIG. 1. A suited piezoelectric material 2 (e.g., Ba-titanate) is in close contact with an adaption layer 1 (e.g. brass or the like) selectively with a similar impedance as the piezoelectric material or with a quite different impedance (e.g., air in order to prevent energy radiation to the rear) and is connected toward the front toward the application side to a Fresnel lens 5 like the one described above or in patent DE 29 19 176. Advantageous is the use of a lens material with an impedance lying between that of the piezoelectric ceramics and that of the connection medium. Possible materials are, e.g., aluminium or even polystyrene. Advantageous is also the use of one of the multiple adapting layers 3,4 which permit low-reflection impedance adaption of the generating material (e.g., piezo ceramics) to the coupling medium (e.g., water) and finally to the corporal tissue. The Fresnel lens itself can serve as the support structure of the entire compound transducer, resulting in little overall weight and easy handling. As FIG. 2 shows, such a Fresnel compound transducer can be combined with a suited locating device 8 for representation and control of the target area 10 as well as with a variable control distance 6 for adaption to varying anatomical conditions.

The use of suited coupling media 6 (e.g., water, US coupling gel, gel disks, or the like) permits adapting the anatomically given space between the applicators and the surface of the body. Coupling medium 6 can, e.g., be confined by a flexible cushion 7.

Figure 3:
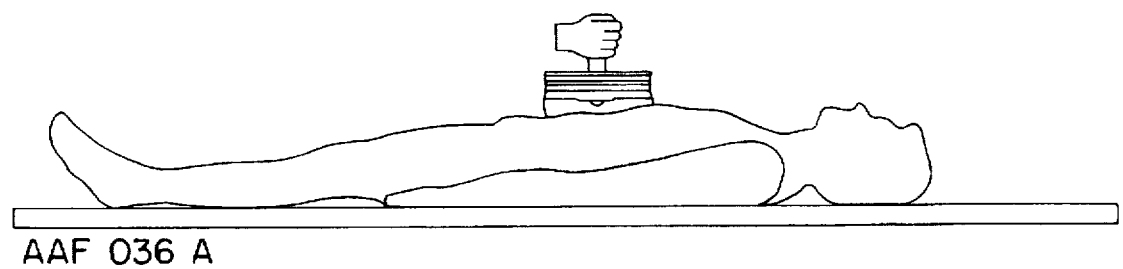
FIG. 3 shows use of the applicator on a patient.

FIG. 3 shows a possible use of such an applicator on a patient.

Due to its flat design, the applicator can be easily placed on the patient's body. The diagnostic ultrasound permits locating the target area: handling is similar to that of a diagnostic ultrasonic -B-image transducer on a patient.

Figure 4A:
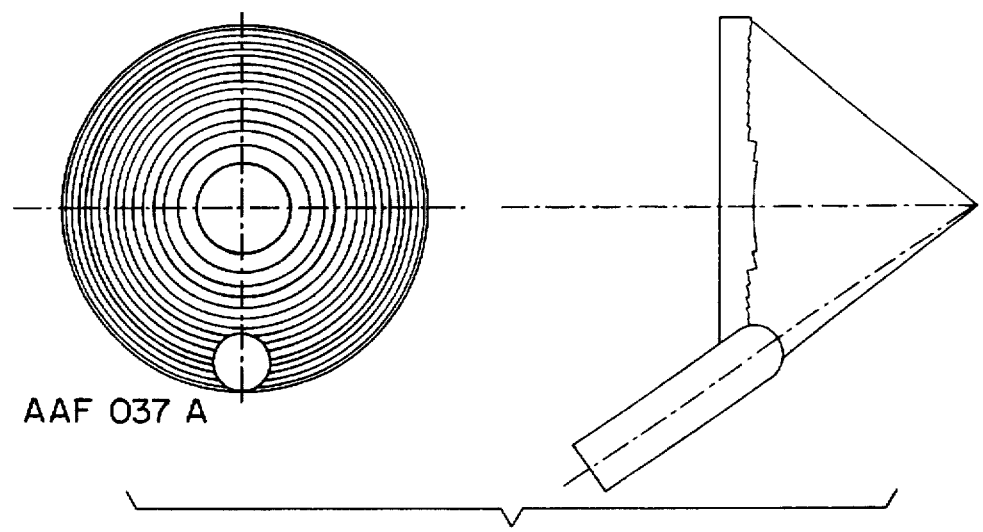
FIGS. 4a, 4b, 4c and 4d show applicators of non-circular outline and their relationship to a target locator.
Figure 4B:
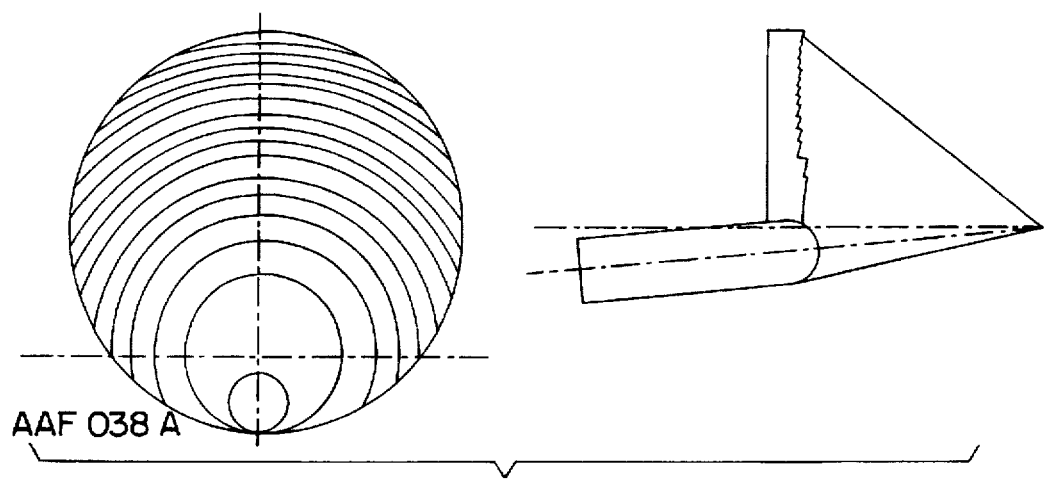
Figure 4C:
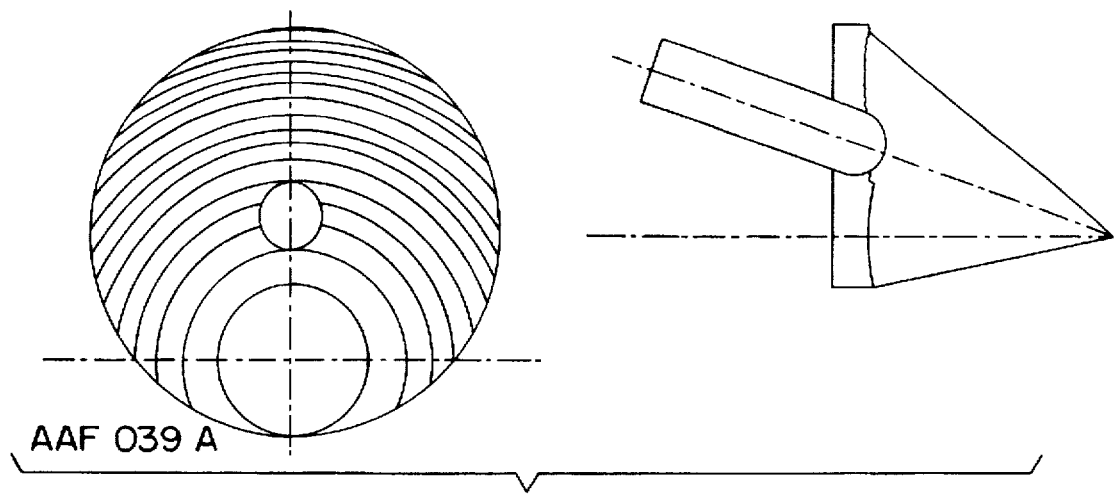
Figure 4D:
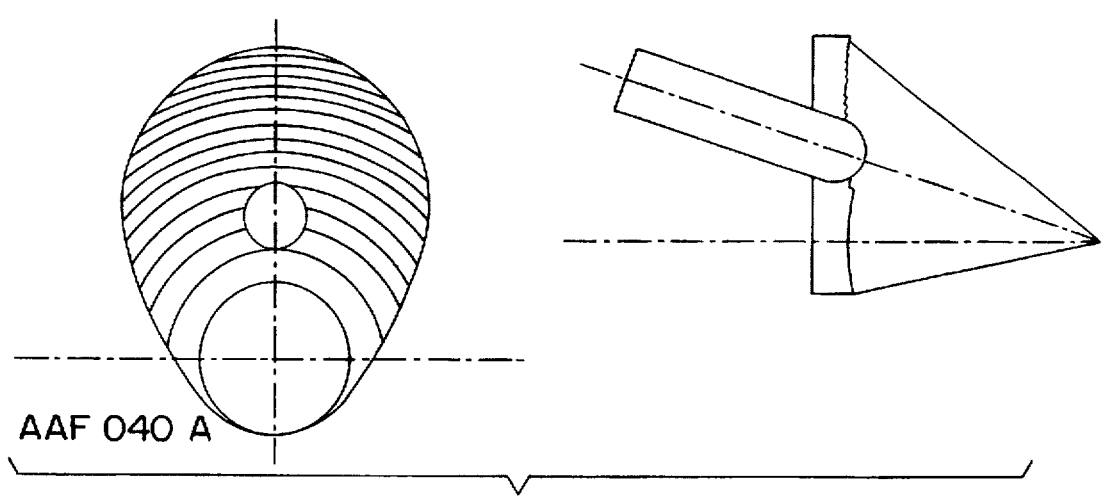

Depending on the anatomical conditions, apart from applicators of circular outline, applicators of any desired shape can also be realized and the position as well as the orientation of the locating component can be varied. Some examples are shown in FIGS. 4a, 4b, 4c and 4d The arrangement shown in FIG. 4c is suited, e.g., for treating anomalies of the prostate gland through the filled urinary bladder with a downward offset beam direction. Other suited applicators which are adapted to the special windows and beam directions can be fixed in almost any desired manner. For instance, energy input can be optimized and adapted to the special anatomical conditions without being tied to the usually circular coupling window predetermined by the device.

Another advantage of the present invention is that when utilizing a wideband transducer the focal distance from the applicator can be changed by varying the excitation frequency. Thus, by raising the ultrasound frequency, the focus can be generated closer to the applicator and by lowering the frequency, it can be shifted farther away.

This "zoom effect" permits treatment without a variable control distance, resulting in advantages with regard to loss-free coupling and low phase disturbances. Improved energy concentration results in improved localized and more effective focal and therapy zones.

Figure 5A:
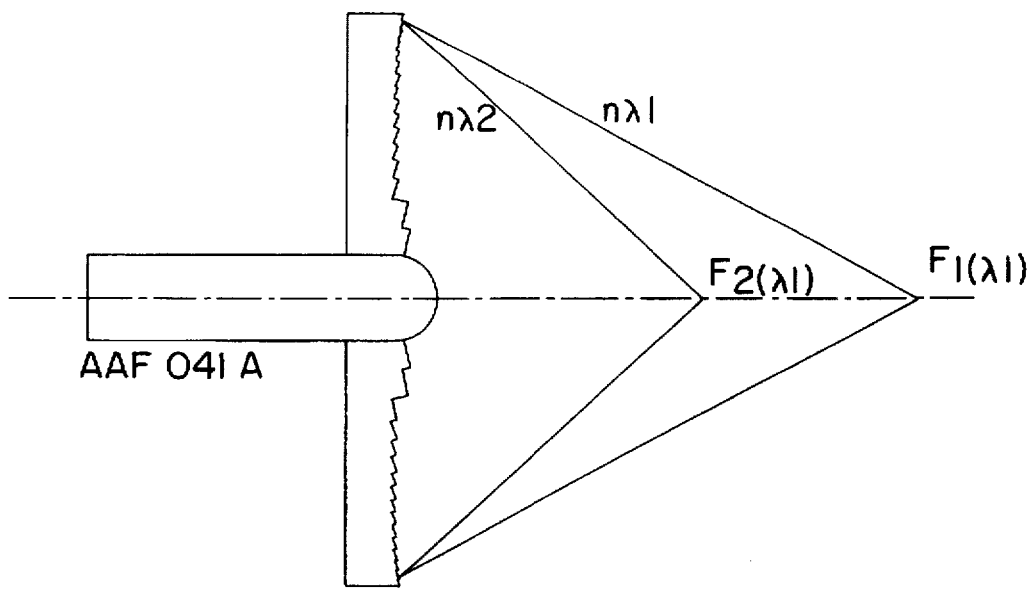
FIG. 5 shows wavelength relationship to various focal depth zones within the body.
Figure 5B:
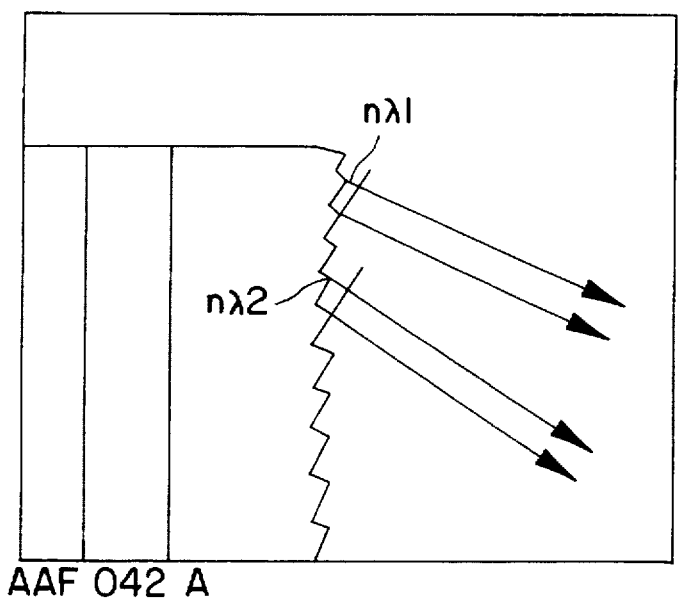

As shown in FIG. 5, various depths in the body zones can be reached from the surface of the body in direct contact of the applicator to the skin.

What is claimed is:

1. An apparatus for the treatment of the human body by means of focussed acoustical waves, comprising:

a sound generating unit shaped so that its generated wave is an essentially plane wave, and having an acoustical impedance, said sound generating unit being triggered by a control unit to generate acoustic waves having a selected specific frequencies and energies;

a rigid focussing unit comprising a Fresnel lens-like structure disposed in a fixed spatial relationship to said sound generating unit whereby said focussing unit focusses the waves generated by said sound generating unit in a desired selected focal range, the material of said focussing unit having an acoustical impedance;

manipulation means attached to said focussing unit for positioning said apparatus relative to a human body;

a coupling medium for coupling said focussing unit to a human body said coupling medium having an acoustical impedance;

the acoustical impedance of said focussing material lying between the acoustical impedance of said sound generating unit and the acoustical impedance of the coupling medium, said coupling medium being situated in the sound path between said focussing unit and said human body, said focussing unit serving as a carrier for the entire structure; and at least one adaption layer positioned between said radiation area of said sound generating unit and of said sound entry area of the focussing unit, the acoustical impedance of said adaption laying between that of said focussing unit and that of the acoustical impedance of said sound generating unit.

2. An apparatus according to claim 1, in which said focussing unit is connected directly to its sound entry area or via at least one adaption layer to the radiation area of said sound generating unit and having with a Fresnel lenslike structure on its sound exit area.

3. An apparatus according to claim 2 in which adaption layer is provided between said radiation area of said sound generating unit and the sound entry surface of said focussing unit having an impedance which lies between that of said focussing unit and the impedance of said sound generating unit.

4. An apparatus according to claim 3, in which said adaption layer is low-reflecting.

5. An apparatus according claim 3, in which said adaption layer is at least partially λ/4 layers.

6. An apparatus according to claim 1 in which said focussing unit is composed of a material the acoustic impedance of which lies between the impedance of said sound generating unit and the impedance of the medium which is situated in the sound path behind said focussing unit.

7. An apparatus according to claim 1, in which at least one said adaption layer is being disposed on the interface of said sound generating unit opposite said radiation area.

8. An apparatus according to claim 7, in which said adaption layer disposed on said opposite interface having either a similar impedance to the one of said sound generating unit or having a very different one.

9. An apparatus according to claim 1 in which said sound generating unit is provided with a piezotransducer.

10. An apparatus according to claim 1, in which said focussing unit serves as the carrier body for the entire structure.

11. An apparatus according to claim 1, in which said sound generating unit is provided with a multiple of individual transducers.

12. An apparatus according to claim 11, in which said individual transducers are arranged mosaic-like.

13. An apparatus according to claim 11, in which said individual transducers have the shape of concentrically disposed rings.

14. An apparatus according to claim 13, in which said rings being constructed like Fresnel zones.

15. An apparatus according to claim 11 in which said control unit triggers said individual transducers separately.

16. An apparatus according to claim 15, in which said control unit triggers said individual transducers with varying phase positions.

17. An apparatus according to claim 15 in which said control unit triggers said individual transducers each with a different frequency.

18. An apparatus according to claim 1, in which a locating device is provided permitting locating a to-be-treated region.

19. An apparatus according to claim 18, in which said locating device is disposed in the central region of said sound exit area of said focussing unit.

20. An apparatus according to claim 18, in which said locating device is disposed outside said central region of said sound exit area of said focussing unit.

21. An apparatus according to claim 18 in which said locating device is provided with an X-ray locating device.

22. An apparatus according to claim 18, in which said locating device is provided with an ultrasonic locating device.

23. An apparatus according to claim 22, in which said ultrasonic locating device is an ultrasonic B-imaging device.

24. An apparatus according to claim 1 in which said sound exit area of said Fresnel lens-like structure having a rotationally symmetrical shape.

25. An apparatus according to claim 1 in which said sound exit area of said Fresnel lenslike structure is a shape adapted to the respective treatment case.

26. An apparatus according to claim 1, in which said control unit varies the frequency with which it triggers said sound generating unit in order to vary the focal position.

27. An apparatus according to claim 1 in which a coupling medium is provided between said sound exit area of said focussing unit and the coupling region of the to-be-treated body.

28. An apparatus according to claim 27, in which said coupling medium is confined by a flexible cushion.

29. An apparatus according to claim 27 in which said coupling medium forms a variable control distance.

* * * * *